(12) United States Patent
Yamamoto et al.

(10) Patent No.: US 7,645,582 B2
(45) Date of Patent: Jan. 12, 2010

(54) **APTAMERS THAT BIND TO *LISTERIA* SURFACE PROTEINS**

(75) Inventors: Cindy Yamamoto, Irvine, CA (US); Toshit Sen, Tustin, CA (US)

(73) Assignees: Hitachi Chemical Co., Ltd., Shinjuku-ku, Tokyo (JP); Hitachi Chemical Research Center Inc., Irvine, CA (US)

( * ) Notice: Subject to any disclaimer, the term of this patent is extended or adjusted under 35 U.S.C. 154(b) by 0 days.

(21) Appl. No.: 12/422,971

(22) Filed: Apr. 13, 2009

(65) Prior Publication Data

US 2009/0203028 A1    Aug. 13, 2009

Related U.S. Application Data

(63) Continuation-in-part of application No. 12/374,480, filed as application No. PCT/US2007/074044 on Jul. 20, 2007.

(60) Provisional application No. 60/832,648, filed on Jul. 21, 2006, provisional application No. 60/876,929, filed on Dec. 22, 2006, provisional application No. 61/044,365, filed on Apr. 11, 2008.

(51) Int. Cl.
*C12Q 1/68* (2006.01)

(52) U.S. Cl. .................... 435/6; 435/91.1; 536/22.1; 536/23.1

(58) Field of Classification Search ................ None
See application file for complete search history.

(56) References Cited

U.S. PATENT DOCUMENTS

| | | | |
|---|---|---|---|
| 5,270,163 | A | 12/1993 | Gold et al. |
| 5,475,096 | A | 12/1995 | Gold et al. |
| 5,756,291 | A | 5/1998 | Griffin et al. |
| 5,792,613 | A | 8/1998 | Schmidt et al. |
| 7,435,542 | B2 | 10/2008 | Shi et al. |
| 2002/0009811 | A1 | 1/2002 | Bodenhamer et al. |
| 2004/0018530 | A1 | 1/2004 | Bowser et al. |
| 2005/0003362 | A1 | 1/2005 | Krylov et al. |
| 2005/0089893 | A1 | 4/2005 | Lopez et al. |
| 2005/0282226 | A1 | 12/2005 | Okada et al. |
| 2006/0008841 | A1 | 1/2006 | Okada et al. |
| 2006/0078901 | A1 | 4/2006 | Buchrieser et al. |
| 2006/0121489 | A1 | 6/2006 | Gorenstein et al. |
| 2007/0207457 | A1 | 9/2007 | Asai et al. |
| 2007/0243529 | A1 | 10/2007 | Li et al. |
| 2008/0182759 | A1 | 7/2008 | West et al. |
| 2008/0286788 | A1 | 11/2008 | James |
| 2009/0004644 | A1 | 1/2009 | Kiel et al. |
| 2009/0029363 | A1 | 1/2009 | Kage |

FOREIGN PATENT DOCUMENTS

| | | |
|---|---|---|
| WO | WO/2006/135527 | 12/2006 |
| WO | WO 2008/011608 | 1/2008 |

OTHER PUBLICATIONS

International Search Report, for corresponding PCT application No. PCT/US07/74044, WIPO, Oct. 1, 2008.
Ellington et al., In vitro selection of RNA molecules that bind specific ligands, *Nature*, 1990, vol. 346, pp. 818-822.
Gopinath et al., An RNA aptamer that distinguishes between closely related human influenza viruses and inhibits haemagglutanin-mediated membrane fusion, *J Gen. Virol.*, 2006, vol. 87, pp. 479-487.
Tuerk et al., Systematic Evolution of Ligands by Exponential Enrichment: RNA Ligands to Bacteriophage T4 DNA Polymerase, *Science*, 1990, vol. 249, pp. 505-510.

*Primary Examiner*—Heather G Calamita
(74) *Attorney, Agent, or Firm*—Knobbe, Martens, Olson & Bear LLP

(57) ABSTRACT

Aptamers bind to *Listeria* surface proteins. A method of assaying a sample for the presence of *Listeria monocytogenes* includes exposing the sample to an aptamer that specifically binds one of the following proteins: *Listeria monocytogenes* internalin A protein, *Listeria monocytogenes* internalin E protein, and *Listeria monocytogenes* 0610 protein. The presence of *Listeria monocytogenes* in the sample is detected when the aptamer binds the protein present in the sample. A method of treating *Listeria monocytogenes* infection includes administering the aptamers to the mammal at a concentration sufficient to reduce *Listeria monocytogenes* infection.

16 Claims, No Drawings

SEQUENCE LISTING

<160> NUMBER OF SEQ ID NOS: 16

<210> SEQ ID NO 1
<211> LENGTH: 45
<212> TYPE: DNA
<213> ORGANISM: Artificial Sequence
<220> FEATURE:
<223> OTHER INFORMATION: Aptamer targeting Listeria monocytogenes InlA
      protein

<400> SEQUENCE: 1
atcatagacc agtaaggggc tattaggtcc cgtaatcagc agagg 45

<210> SEQ ID NO 2
<211> LENGTH: 45
<212> TYPE: DNA
<213> ORGANISM: Artificial Sequence
<220> FEATURE:
<223> OTHER INFORMATION: Aptamer targeting Listeria monocytogenes InlA protein

<400> SEQUENCE: 2
atcgtaccat aacattatat agatgtcttg ttttcgcagg aatcg 45

<210> SEQ ID NO 3
<211> LENGTH: 45
<212> TYPE: DNA
<213> ORGANISM: Artificial Sequence
<220> FEATURE:
<223> OTHER INFORMATION: Aptamer targeting Listeria monocytogenes InlA protein

<400> SEQUENCE: 3
atcaatccga tgtcgttata ctatgtgtca ttccgtaaca gccag 45

<210> SEQ ID NO 4
<211> LENGTH: 47
<212> TYPE: DNA
<213> ORGANISM: Artificial Sequence
<220> FEATURE:
<223> OTHER INFORMATION: Aptamer targeting Listeria monocytogenes InlA protein

<400> SEQUENCE: 4
atccatgggg cggagatgag ggggaggagg gcgggtaccc ggttgat 47

<210> SEQ ID NO 5
<211> LENGTH: 45
<212> TYPE: DNA
<213> ORGANISM: Artificial Sequence
<220> FEATURE:
<223> OTHER INFORMATION: Aptamer targeting Listeria monocytogenes Lmo0610 protein

<400> SEQUENCE: 5
atcggttact gaagcatatg tccgggggat tgccaagcct tcccg 45

<210> SEQ ID NO 6
<211> LENGTH: 45
<212> TYPE: DNA
<213> ORGANISM: Artificial Sequence
<220> FEATURE:
<223> OTHER INFORMATION: Aptamer targeting Listeria monocytogenes InlE protein

<400> SEQUENCE: 6
atcggcttgc cattgtaagc cattccaaca ttccacgtac gatgg    45

<210> SEQ ID NO 7
<211> LENGTH: 45
<212> TYPE: DNA
<213> ORGANISM: Artificial Sequence
<220> FEATURE:
<223> OTHER INFORMATION: Aptamer targeting Listeria monocytogenes InlE
      protein

<400> SEQUENCE: 7
atcgatgatc tggtcgccgt aacactaccc acatatacga ccagg    45

<210> SEQ ID NO 8
<211> LENGTH: 45
<212> TYPE: DNA
<213> ORGANISM: Artificial Sequence
<220> FEATURE:
<223> OTHER INFORMATION: Aptamer targeting Listeria monocytogenes InlE protein

<400> SEQUENCE: 8
atcgggggcg gtgtcggagc acatctaatg tcgtttcgtg tccgg 45

<210> SEQ ID NO 9
<211> LENGTH: 33
<212> TYPE: DNA
<213> ORGANISM: Artificial Sequence
<220> FEATURE:
<223> OTHER INFORMATION: InlA Sense Primer

<400> SEQUENCE: 9
ggtattgagg gtcgcacaaa tgctcaggca gct 33

<210> SEQ ID NO 10
<211> LENGTH: 38
<212> TYPE: DNA
<213> ORGANISM: Artificial Sequence
<220> FEATURE:
<223> OTHER INFORMATION: InlA Antisense Primer

<400> SEQUENCE: 10
agaggagagt tagagcctta tgaagcttct tttgaatt 38

<210> SEQ ID NO 11
<211> LENGTH: 33
<212> TYPE: DNA
<213> ORGANISM: Artificial Sequence
<220> FEATURE:
<223> OTHER INFORMATION: InlE Sense Primer

<400> SEQUENCE: 11
ggtattgagg gtcgcgtaca agcagcggtg att 33

<210> SEQ ID NO 12
<211> LENGTH: 39
<212> TYPE: DNA
<213> ORGANISM: Artificial Sequence
<220> FEATURE:
<223> OTHER INFORMATION: InlE Antisense Primer

<400> SEQUENCE: 12
agaggagagt tagagcctta cagattattt attccttcg 39

<210> SEQ ID NO 13

-continued

```
<211> LENGTH: 35
<212> TYPE: DNA
<213> ORGANISM: Artificial Sequence
<220> FEATURE:
<223> OTHER INFORMATION: Lmo0610 Sense Primer

<400> SEQUENCE: 13
ggtattgagg gtcgcgctca agatgttgtc aacat                              35

<210> SEQ ID NO 14
<211> LENGTH: 38
<212> TYPE: DNA
<213> ORGANISM: Artificial Sequence
<220> FEATURE:
<223> OTHER INFORMATION: Lmo0610 Antisense Primer

<400> SEQUENCE: 14
agaggagagt tagagcctta agatttcgca gattgtcc                           38

<210> SEQ ID NO 15
<211> LENGTH: 18
<212> TYPE: DNA
<213> ORGANISM: Artificial Sequence
<220> FEATURE:
<223> OTHER INFORMATION: LIC-F Primer

<400> SEQUENCE: 15
ggtattgagg gtcgcatc                                                 18

<210> SEQ ID NO 16
<211> LENGTH: 20
<212> TYPE: DNA
<213> ORGANISM: Artificial Sequence
<220> FEATURE:
<223> OTHER INFORMATION: Biotinylated LIC-R Primer

<400> SEQUENCE: 16
agaggagagt tagagccatc                                               20
```

APTAMERS THAT BIND TO *LISTERIA* SURFACE PROTEINS

CROSS-REFERENCE TO RELATED APPLICATIONS

This application claims priority to U.S. Provisional Patent Application No. 61/044,365, filed on Apr. 11, 2008, and is a continuation-in-part of U.S. patent application Ser. No. 12/374,480, entered into the national phase on Jan. 20, 2009, which is the U.S. national phase of International Patent Application No. PCT/US2007/074044, filed on Jul. 20, 2007, which was published in English as WO 2008/011608 on Jan. 24, 2008, and claims priority to U.S. Provisional Patent Application Nos. 60/832,648 and 60/876,929, filed on Jul. 21, 2006 and Dec. 22, 2006 respectively. All of the foregoing applications are hereby incorporated by reference.

BACKGROUND

1. Field of the Invention

The present disclosure relates to novel nucleic acid ligands (aptamers) that bind to the *Listeria* outer membrane protein targets internalin A (InlA; Lmo0433), internalin E (InlE; Lmo0264), and Lmo0610. The disclosed aptamer reagents can be used to screen samples such as food, clinical, and environmental samples for the presence of InlA, InlE, and Lmo0610. The novel DNA aptamers can also potentially be used in various applications in which the presence or absence of *Listeria* is required.

2. Description of the Related Art

An estimated 76 million foodborne illnesses occur each year in the United States, resulting in 325,000 hospitalizations and 5000 deaths (see Mead et al., "Food-Related Illness and Death in the United States," *Emerg. Infec. Dis.* 5, 607-25 (1999)). *Listeria monocytogenes* has been implicated in at least 11 human foodborne epidemics worldwide and is associated with foods that are ready-to-eat and can be consumed without cooking (see Ben Embarek, P. K., "Presence, Detection and Growth of *Listeria Monocytogenes* in Seafoods: a review," *Int. J. Food Microbiol.* 23, 17-34 (1994)). Although *Listeria monocytogenes* causes only 2500 cases of foodborne illness per year, it is responsible for 10% of the total foodborne illness-related deaths. The majority of human listeriosis cases occur in neonates, the elderly, and immuno-compromised individuals, with case fatality rates of 20-40% (see Farber et al., "*Listeria monocytogenes*, a Food-Borne Pathogen," *Microbio. Rev.* 55, 476-511 (1991); Schuchat et al., "Epidemiology of Human Listeriosis," *Clin. Microbiol. Rev.* 4, 169-83 (1991); "Update—Multistate Outbreak of Listeriosis," *Centers for Disease Control & Prevention Morbid. Mortal. Weekly Rep.* 47, 1117-18 (1999); Jacquet et al., "Investigations related to the epidemic strain involved in the French Listeriosis outbreak in 1992," *Appl. Environ. Microbiol.* 61, 2242-46 (1995)). Because of the severity of the illness and its association with foods that can be consumed without heating, the U.S. Food and Drug Administration (FDA) and Food Safety and Inspection Service (FSIS) established a zero tolerance policy for the presence of *Listeria monocytogenes* in ready-to-eat (RTE) foods in 1989.

The increasing number of governmental regulations and the changing topography of food processing and manufacturing have spurred the development of faster, more sensitive, and cost-effective technologies for pathogen detection. Currently, there are many different methods available for *Listeria monocytogenes* and *Listeria* spp. detection on the market. The most widely used method, due to cost and sensitivity considerations, is the traditional microbiological method of plating. Although the currently available methods are effective for recovery of *Listeria monocytogenes* from a variety of samples, positive results are not obtained until 5-7 days after sample collection. Rapid methods that employ nucleic acid amplification and immunochemical techniques reduce the time needed to obtain results compared to culture-based methods and offer the possibility of high throughput automation. The rapid methods currently on the market comprise PCR, probe hybridization, enzyme-linked immunoassay (ELISA), enzyme-linked fluorescent assay (ELFA), lateral flow, and magnetic bead-based methods. The time needed to obtain results decreases to 2-4 days for these assays, but most require enrichment steps to improve sensitivity and allow recovery of injured or stressed organisms.

The faster time-to-results and high throughput capabilities have led to increased adoption of PCR methods in food testing, but the greater costs associated with use of PCR methods as compared to traditional culture methods and their lack of universal acceptance currently restricts the widespread use of molecular methods in general. PCR-based methods also have several limitations. Theoretically, PCR-based technology should provide the detection level of $\leq 1$ CFU/25 g food sample mandated by the zero tolerance regulation. Assay sensitivity, however, is complicated by a number of factors, including low contamination levels, large sample volumes relative to reaction volumes, and inhibition of the PCR reaction by components of the food matrix. Thus assay sensitivities typically do not reach theoretical values (see Norton, D. M., *J. AOAC Int.* 85, 505-15 (2002)). Also, PCR only detects the presence of DNA and cannot indicate whether the pathogens are dead or alive.

By contrast, immunological methods rely on the interaction between specific antibodies to selectively capture, label, or detect a target organism and are widely used and accepted for the detection and confirmation of specific microorganisms. The widespread use and acceptance of immunology-based methods has resulted in a vast array of commercial test kits for the detection of the most common foodborne bacteria in foods, including *Salmonella*, *Listeria*, *Campylobacter*, and *E. coli* O157:H7. ELISAs, which are the most common format used for immunological detection, have detection limits of between $10^3$-$10^5$ cfu/mL (see Churchill et al., "Detection of *Listeria monocytogenes* and the toxin listeriolysin O in food," *J. Microbiol. Meth.* 64, 141-70 (2006)). To achieve this detection limit often requires enrichment of the pathogens for at least 24 hours before the sample is adequate for detection by ELISA (see de Boer et al., "Methodology for detection and typing of food borne microorganisms," *Int. J. Food Microbiol.* 50, 119-30 (1999)).

Despite the improved time-to-results of many rapid detection systems, the requirement of conventional cultural enrichment still remains an important limiting feature of these methods. Also, these methods lack the ability to detect biomolecules in real time. There is an increasing demand for simple, inexpensive, and reliable tests to analyze food samples. Biosensor technology has the potential to meet these needs in or near real time (see Alocilja et al., "Market analysis of biosensors for food safety," *Biosensors & Bioelectronics* 18, 841-46 (2003); Hall, "Biosensor technologies for detecting microbiological food borne hazards," *Microbes & Infection* 4, 425-32 (2002); Deisingh et al., "Biosensors for the detection of bacteria," *Can. J. Microbiol.* 50, 69-77 (2004)). Studies have shown that biosensors can detect a broad spectrum of analytes in complex samples with minimal sample pre-treatment (see Hall, "Biosensor technologies for detecting microbiological food borne hazards," *Microbes & Infec-* tion 4, 425-432 (2002); Deisingh et al., "Biosensors for the detection of bacteria," *Can. J. Microbiol.* 50, 69-77 (2004)).

Biosensors for bacterial detection generally involve a biological recognition component such as receptors, nucleic acids, or antibodies in contact with physical or chemical transducers. Depending on the method of signal transduction, biosensors can be divided into five basic types: electrochemical, optical, piezoelectric, thermal, and magnetic. Recently, sensors have been developed for detection of *Listeria monocytogenes* (see Geng et al., "Detection of Low Levels of *Listeria monocytogenes* Cells by Using a Fiber-Optic Immunosensor," *Applied & Environmental Microbiology* 70, 6138-46 (2004); Leonard, P. et al., *J. Food Prot.* 68, 728-35 (2005); Leonard et al., "A generic approach for the detection of whole *Listeria monocytogenes* cells in contaminated samples using surface Plasmon resonance," *Biosensors & Bioelectronics* 19, 1331-35 (2004); Tims, T. B. et al., "Detection of low levels of *Listeria monocytogenes* within 20 hours using an evanescent wave biosensor," *Am. Clin. Lab.* 20, 28-29 (2001)). The sensitivity and specificity of these assays are dependent on the specific antibody that is used for detection. The sensitivity threshold for a fiber-optic immunosensor (Analyte 2000; Research International, Woodinville, Wash.) was measured to be approximately $10^3$ CFU/mL for a pure culture of *Listeria monocytogenes* and $10^4$ CFU/mL when grown with lactic acid bacteria (Geng et al., "Detection of Low Levels of *Listeria monocytogenes* Cells by Using a Fiber-Optic Immunosensor," *Applied & Environmental Microbiology* 70, 6138-46 (2004)). These levels of detection compare with immunological methods, as expected, since antibodies were the capture agents in contact with the transducer. Both polyclonal and monoclonal antibodies have been used for biosensor studies. Polyclonal antibodies have been used as detection reagents for several decades (see Breitling, F., Dubel, S. *Recombinant Antibodies* 154 (John Wiley & Sons Inc. 1999)). The supply of polyclonal antibodies is limited and repeated immunizations are required to replenish depleted stocks. By contrast, monoclonal antibodies offer a continuous supply of homogeneous, well-characterized antibodies. High cost, low yields, and the requirement of skilled labor are some of the problems associated with monoclonal antibody production.

Aptamers, first reported in 1990 (see Tuerk, C., Gold, L., *Science* 249, 505-10 (1990); Ellington et al., "In vitro selection of RNA molecules that bind specific ligands," *Nature* 346, 818-22 (1990)), offer ideal candidates for use as the biological recognition components in biosensors, possessing advantages over traditional antibodies for use in sensors (see Jayasena, "Aptamers: An Emerging Class of Molecules That Rival Antibodies in Diagnostics," *Clin. Chem.* 45, 1628-50 (1990)). Aptamers are nucleic acid ligands that can be generated against amino acids, drugs, proteins, and complex targets such as cells (see Gopinath, S. C. et al., "An RNA aptamer that distinguishes between closely related human influenza viruses and inhibits hemagglutinin-mediated membrane fusion," *J. Gen. Virol.* 87, 479-487 (2006); Cerchia, L. et al., "Neutralizing Aptamers from Whole-Cell SELEX Inhibit the RET Receptor Tyrosine Kinase," *PLoS Biol.* 3, e123 (2005); Duconge, F. et al., *PLos Biol.* 3, e123 (2005); Mori, T. et al., "RNA aptamers selected against the receptor activator of NF-kB acquire general affinity to proteins of the tumor necrosis factor receptor family," *Nuc. Acids Res.* 32, 6120-28 (2004); Daniels, D. A. et al., "A tenascin-C aptamer identified by tumor cell SELEX: Systematic evolution of ligands by exponential enrichment," *Proc. Natl. Acad. Sci.* 100, 15416-21 (2003)). Numerous aptamers have been selected using this technique against a wide range of targets, with selectivity, specificity, and affinity equal and sometimes superior to those of antibodies. The technique in which these oligonucleotide ligands are obtained was termed SELEX (Systematic Evolution of Ligands by Exponential Enrichment), described in U.S. Pat. Nos. 5,475,096 and 5,270,163. The advantages of using aptamers over traditional antibodies for in vitro assays include: 1) the ability to be denatured/renatured multiple times (reusable), 2) stability in long term storage and the ability to be transported at ambient temperature, 3) the ability to adjust selection conditions to obtain aptamers with properties desirable for in vitro assay, 4) generation by chemical synthesis, resulting in little batch to batch variation, 5) selection through an in vitro process eliminating the use of animals, and 6) the ability to attach reporter molecules at precise locations (see O'Sullivan, C. K., "Aptasensors—the future of biosensing?" *Anal. Bioanal. Chem.* 372, 44-48 (2002)).

Aptamers have yet to be used in diagnostic or biosensor approaches for food-borne pathogen detection. The aptamers isolated against outer membrane proteins in *Listeria* may be used in diagnostic and biosensor detection technologies for food, clinical, or environmental samples.

SUMMARY

An embodiment provides a method of assaying a sample for the presence of *Listeria monocytogenes*, comprising exposing the sample to an aptamer that specifically binds a protein selected from the group consisting of *Listeria monocytogenes* internalin A protein, *Listeria monocytogenes* internalin E protein, and *Listeria monocytogenes* 0610 protein, and determining that *Listeria monocytogenes* is present in the sample when the aptamer binds the protein present in the sample.

Another embodiment provides a method of treating *Listeria monocytogenes* infection in a mammal, comprising administering to the mammal an aptamer that specifically binds a protein selected from the group consisting of *Listeria monocytogenes* internalin A protein, *Listeria monocytogenes* internalin E protein, and *Listeria monocytogenes* 0610 protein at a concentration sufficient to reduce *Listeria monocytogenes* infection.

In a further aspect, the aptamer comprises a sequence of one of SEQ ID NOs: 1-8.

DETAILED DESCRIPTION OF THE PREFERRED EMBODIMENTS

The present disclosure relates to the isolation of novel reagents selected for their binding characteristics to the proteins InlA, InlE, and Lmo0610. InlA is a 744 amino acid protein and belongs to a large internalin multigene family identified in the *Listeria* genome. InlA enables *Listeria monocytogenes* to invade non-phagocytic cells such as those of the human intestinal epithelium (see Gaillard, J. L. et al., "Entry of *L. monocytogenes* into Cells Is Mediated by Internalin, a Repeat Protein Reminiscent of Surface Antigens from Gram-Positive Cocci," *Cell* 65, 1127-41 (1991)) and is sufficient for adhesion to and inducing uptake into epithelial cells (see Schubert, W. D. et al., "Structure of Internalin, a Major Invasion Protein of *Listeria monocytogenes*, in Complex with its Human Receptor E-Cadherin," *Cell* 111, 825-36 (2002)). Besides InlB and InlC, the roles of proteins encoded by other members of the internalin gene family are not very well understood. InlE is a 499 amino acid protein and also belongs to the internalin multigene family, displaying all of the characteristic features such as a signal sequence, two regions of repeats (LRR and B), and a putative C-terminal cell wall anchor. The specific function of this internalin, however, remains unclear. Isogenic deletion mutants in InlC2, InlD, InlE, and InlF showed no reduction in invasion of several cell lines, indicating that these genes are not required for the entry of *L. monocytogenes* into these cells (Dramsi, S. et al., "Identification of Four New Members of the Internalin Multigene Family of *Listeria monocytogenes* EGD," *Infection & Immunity*, 1615-25 (May 1997)). In a similar study, a ΔINlGHE mutant showed no reduction in invasiveness for the Caco-2 cell line but showed significantly reduced virulence after oral infection of mice (Raffelsbauer, D. et al., "The gene cluster InlC2DE of *Listeria monocytogenes* contains additional new internalin genes and is important for virulence in mice," *Mol. Gen. Genet.* 260, 144-58 (1998)). Similarly to InlE, very little information is known about the Lmo0610 protein. The Lmo0610 protein was identified during an analysis of the *Listeria* cell wall proteome using two-dimensional chromatography coupled to mass spectrometry (Calvo, E. et al., "Analysis of the *Listeria* cell wall proteome by two-dimensional nanoliquid chromatography coupled to mass spectrometry," *Proteomics* 5, 433-43 (2005)). This 553 amino acid protein was among those identified in cell wall extracts of the genome strains *L. monocytogenes* EGD-e bearing an LPXTG motif recognized for covalent anchoring to peptidoglycan. Lmo0610 has an unknown function and no known ortholog in *L. innocua*.

The disclosed nucleic acid ligands corresponding to InlA, InlE, and Lmo0610 may be useful for determining the presence or absence of InlA, InlE, Lmo0610, or *Listeria* in food, clinical, or environmental samples. One object is to incorporate these nucleic acid ligands into an in vitro diagnostic or biosensor platform designed to detect the presence or absence of InlA, InlE, Lmo0610, or *Listeria* in food, environmental, or clinical samples.

Table 1 is a list of selected aptamer sequences from in vitro selection screens for InlA, InlE, and Lmo0610. These sequences were selected based on their performance in ELISA and magnetic bead capture experiments for their ability to bind either the targeted protein or *Listeria monocytogenes*.

Disclosed are oligonucleotides that bind the InlA, InlE, and Lmo0610 proteins. Specific oligonucleotide sequences of aptamers specific to InlA, Lmo0610, and InlE are shown in Table 1 as SEQ ID NOs: 1-4, 5, and 6-8 respectively (as indicated in the "Target Protein" column of Table 1). These oligonucleotides could be useful as biological recognition elements in biosensor platforms and/or in vitro diagnostic assays. The oligonucleotides relevant to InlA, InlE, and Lmo0610 comprise 45 or 47 nucleotides. The oligomers comprise nucleotides, modified nucleotides, or a combination thereof. Modified nucleotides can include, but are not limited to, the addition of biotin, thio, iodo, bromo, phosphor, fluoro, or amino groups. Preferably, the oligonucleotides are DNA, but they can also be RNA or synthetic nucleotide analogs. If the oligonucleotides are to be used in biosensor applications, 5', 3', or internal modifications to the nucleotides can be used to bind the oligonucleotides to an electrochemical, optical, piezoelectric, magnetic, or calorimetric biosensor platform. To achieve maximum activity in some embodiments, the disclosed oligonucleotides may employ a spacer when coupled to a solid support such as magnetic beads, columns, and microtiter plates. The spacer may comprise one or more atoms that separate the solid support from the oligomer, where the number of atoms in the spacer is defined as the smallest number of atoms that separates the solid support from the oligomer. For this definition, atoms that do not actually separate the oligomer from the solid support, such as those in side chains rather than in the molecular backbone, are not considered. Thus, for example, the spacer may be a standard 6-atom spacer or a 15-atom spacer such as TEG (tetraethylene glycol). Accordingly, spacers having any number of atoms separating the solid support from the oligomers can be employed, such as 4-, 5-, 6-, 7-, 8-, 9-, 10-, 11-, 12-, 13-, 14-, 15-, 16-, 17-, 18-, 19-, 20-, 21-, 22-, 23-, 24-, or 25-atom spacers.

Aptamer Selection for Internalin A, Internalin E, and Lmo0610

1. Preparation of the Recombinant Proteins

Bacterial DNA coding for *Listeria monocytogenes* protein Internalin A (residues 30-766), Internalin E (residues 30-454) and Lmo0610 (residues 33-539) was PCR amplified from genomic DNA (ATCC #19115D). The primers were designed with Web Primer (genome-www2.stanford.edu/cgi-bin/SGD/web-primer) using the sequences from Genbank Accession Numbers CAC98512, CAD00791 and CAC98688 respectively. The following Table 2 shows the primers for each gene product:

TABLE 1

| Target Protein | Clone | Base Pairs | Sequence (5'-3') | SEQ ID NO |
|---|---|---|---|---|
| In1A (Lmo 0433) | 0433.16 | 45 | ATCATAGACCAGTAAGGGGCTATTAGGTCCCGTAATCAGCAGAGG | 1 |
| In1A (Lmo 0433) | 0433.21 | 45 | ATCGTACCATAACATTATATAGATGTCTTGTTTTCGCAGGAATCG | 2 |
| In1A (Lmo 0433) | 0433.26 | 45 | ATCAATCCGATGTCGTTATACTATGTGTCATTCCGTAACAGCCAG | 3 |
| In1A (Lmo 0433) | 0433.08 | 47 | ATCCATGGGGCGGAGATGAGGGGGAGGAGGGCGGGTACCCGGTTGAT | 4 |
| Lmo 0610 | 0610.2 | 45 | ATCGGTTACTGAAGCATATGTCCGGGGGATTGCCAAGCCTTCCCG | 5 |
| In1E (Lmo 0264) | 0264.1 | 45 | ATCGGCTTGCCATTGTAAGCCATTCCAACATTCCACGTACGATGG | 6 |
| In1E (Lmo 0264) | 0264.3 | 45 | ATCGATGATCTGGTCGCCGTAACACTACCCACATATACGACCAGG | 7 |
| In1E (Lmo 0264) | 0264.10 | 45 | ATCGGGGGCGGTGTCGGAGCACATCTAATGTCGTTTCGTGTCCGG | 8 |

TABLE 2

| | | |
|---|---|---|
| InlA Sense | 5' GGTATTGAGGGTCGCACAAATGCTCAGGCAGCT | SEQ ID NO:9 |
| InlA Antisense | 5' AGAGGAGAGTTAGAGCCTTATGAAGCTTCTTTTGAATT | SEQ ID NO:10 |
| InlE Sense | 5' GGTATTGAGGGTCGCGTACAAGCAGCGGTGATT | SEQ ID NO:11 |
| InlE Antisense | 5' AGAGGAGAGTTAGAGCCTTACAGATTATTTATTCCTTCG | SEQ ID NO:12 |
| Lmo0610 Sense | 5' GGTATTGAGGGTCGCGCTCAAGATGTTGTCAACAT | SEQ ID NO:13 |
| Lmo0610 Antisense | 5' AGAGGAGAGTTAGAGCCTTAAGATTTCGCAGATTGTCC | SEQ ID NO:14 |

The 5' (underlined) region of the primers includes sequences required for a Ligation Independent Cloning (LIC) strategy. The PCR products were treated for LIC cloning and inserted in-frame downstream from the His-tag sequence in the pET-30 Xa/LIC vector (Novagen). The nucleotide sequence of the cloned inserts was verified by sequencing. For expression of the recombinant protein, the resulting plasmids carrying InlA, InlE, or Lmo0610 genes were transformed into the *Escherichia coli* strain BL21 (DE3) plysS.

2. Purification of Recombinant Proteins

*E. coli* BL21 (DE3) plysS transformed with pET30/InlA, pET30/InlE, or pET30/0610 was grown at 37° C. until it reached an OD600 of 0.7 and then was induced with 1 mM IPTG for 3 hours. The induced bacteria were harvested by centrifugation and the pellet was kept at −20° C. overnight. The pellet was re-suspended in 5.0 mL of a solution comprising 50 mM sodium phosphate buffer pH 8.0, 150 mM sodium chloride containing 1 µL lysozyme (EMD Biosciences), 5 µL Benzonase nuclease (EMD Biosciences), 50 µL Sigma P1 protease inhibitor, 1 mM DTT, and 0.01% Triton-X-100. The cell suspension was incubated at room temperature for 10 minutes. Cell debris was removed by centrifugation and the protein was purified by metal affinity chromatography using Ni Sepharose 6 fast flow. A solution comprising 50 mM sodium phosphate buffer pH 8.0, 150 mM sodium chloride, and 20 mM imidazole was used to wash the column, and the bound protein was eluted with 5 mL of a solution comprising 50 mM sodium phosphate buffer pH 8.0, 300 mM sodium chloride, and 500 mM imidazole. The proteins were desalted using a Pierce D-Salt column and the proteins were eluted in a solution comprising 50 mM Tris pH 8.0 and 150 mM sodium chloride by exchanging the buffer during desalting.

The proteins were loaded on a UNO-Q 1 column (Bio-Rad) equilibrated in a solution comprising 50 mM Tris pH 8.0 and 150 mM sodium chloride at room temperature, and were eluted with a linear gradient of 0.15-1 M sodium chloride in the same buffer. Fractions were analyzed by SDS-polyacrylamide gel electrophoresis and quantified by the BioRad protein assay before storage at −80° C.

3. In Vitro Selection of Aptamers

In one embodiment, aptamers to the specified target proteins InlA, InlE, and Lmo0610 were isolated using an in vitro selection procedure. A filter plate was used to separate the aptamer bound to the target protein from aptamer(s) not bound to the target protein. Alternatively, Ni-coated magnetic beads were used to separate the aptamer bound to the target protein from aptamer(s) not bound to the target protein, as disclosed in U.S. patent application Ser. No. 12/374,480 (published in English as WO 2008/011608), previously incorporated herein by reference. The bound aptamer was eluted from the filter plate using an NaOH solution. When magnetic beads were used, the bound aptamer-protein complex was eluted using an imidazole solution. Other methods of destabilizing DNA-protein interactions that are known in the art are also suitable for elution. The eluted aptamer was amplified by PCR using the following primers: LIC-F (5'-ggtattgagggtcgcatc-3'; SEQ ID NO:15) and biotinylated LIC-R (5'-agaggagagttagagccatc-3'; SEQ ID NO:16). The non-biotinylated aptamer strand was isolated using streptavidin-coated magnetic particles according to a method described previously (Murphy, M. B. et al., "An improved method for the in vitro evolution of aptamers and applications in protein detection and purification," *Nuc. Acids Res.* 31, e110 (2003)). The isolated aptamer strand was then used for a subsequent round of in vitro selection. These steps were iterated a sufficient number of times to result in identification of at least one aptamer sequence having high affinity for the target protein.

In other embodiments, aptamers are selected using one or more of the methods disclosed in U.S. Pat. Nos. 7,435,542 and 5,792,613, U.S. Patent Application Publication Nos. 2007/0207457, 2009/0029363, 2007/0243529, 2006/0008841, 2005/0282226, 2008/0286788, 2005/0089893, 2009/0004644, 2005/0003362, 2004/0018530, 2009/011855, and 2008/0182759, and International Patent Application Publication No. WO 2006/135527, all of which are incorporated herein by reference.

In another embodiment, aptamers are selected using a method involving enzymatic cleavage of target bound and unbound oligonucleotides and does not involve the amplification step of typical in vitro selection technologies. A library of oligonucleotides is provided, wherein the oligonucleotides are tagged at one end with either a conserved sequence or label like biotin. The oligonucleotides in the library are then incubated with the target molecule. Optimally, the target molecule is provided in low concentration. The oligonucleotide library is then treated with a 3' to 5' exonuclease or other nuclease that will cleave single stranded oligonucleotides, resulting in cleavage of the oligonucleotides from the one available end only. In this step, the oligonucleotides that are bound to the target protein are protected and the free unbound oligonucleotides are cleaved and subsequently removed. This step is carried out in solution or on a solid support such as a column. The selected uncleaved sequences are then cloned using standard techniques and sequenced for subsequent screening. The labeled end or conserved sequence at the 5' end facilitates this step. Since proteins that are more tightly bound to the DNA are more resistant to exonuclease cleavage, this procedure identifies aptamer sequences having a high affinity for the target protein.

4. ELISA Screening of Aptamers

The methods for selecting aptamer sequences that are disclosed above generate many clones that contain possible oligonucleotides with a high affinity to the specified target protein. In one embodiment, the relative binding strength of the isolated clones to the target protein was screened using ELISA. A nickel-coated microplate (HisSorb, Qiagen) was used to bind 500 ng his-tagged InlA, InlE, or Lmo0610 to the plate as per manufacturer's directions. Biotinylated aptamers (5 ng/μL) were heated to 95° C. for 3 minutes and quickly cooled to 4° C. for 5 minutes before application to each well. The biotinylated aptamers were incubated with the bound proteins in the HisSorb plate overnight at 4° C. with gentle shaking. Wells were then washed four times with 200 μL PBS-T. Streptavidin-horseradish peroxidase was added to the wells for 30 minutes at room temperature with gentle shaking. The wells were washed as described previously before development with TMB (Pierce). The reactions were stopped with 1 M $H_2SO_4$ and absorbance was measured at 450 nm using a ThermoMax microplate reader (Molecular Devices).

Magnetic Bead Capture of *Listeria monocytogenes*

The disclosed aptamers were tested for their ability to capture *Listeria monocytogenes* when coupled to magnetic beads.

In one embodiment, biotinylated aptamers were tested for *Listeria monocytogenes* capture by coupling them to nanomagnetic streptavidin beads followed by plating on chromogenic agar. Capture efficiencies were highest when the aptamers were bound to 300 nm beads as compared to larger magnetic beads such as 500 nm, 1 μm, and 2.8 μm beads. Thus in one embodiment, the bead diameter is between 50 nm and 500 nm. In another embodiment, the bead diameter is between 200 nm and 400 nm. In another embodiment, 20 μL of 300 nm streptavidin-plus magnetic beads (Ademtech) were washed once in 200 μL 2×BW buffer (10 mM Tris-HCl pH 7.5, 1 mM EDTA, 2.0 M NaCl). The beads were re-suspended in 40 μL 2×BW buffer. An equal volume of 200 μmol biotinylated aptamer was then added and incubated for 15 minutes at room temperature. For increased activity, a 15-atom spacer such as TEG (tetraethylene glycol) may be inserted into the aptamer at the location which attaches to the solid support, such as the 5' or 3' end, or internally. These coupled beads were washed 2 times with 1 mL PBS-T. The beads were allowed to pellet in a magnetic stand (MPC; Invitrogen) for 3 minutes during the wash steps. Following the last wash, the beads were re-suspended in 20 μL PBS-T and stored at 4° C. until use. Before use, the beads were heat denatured at 90° C. for 3 minutes and placed on ice before using.

An overnight culture of *L. monocytogenes* was grown in BHI at 37° C. for the *Listeria monocytogenes* capture experiments. Based on plate counts, a $1\times10^4$ cfu/mL dilution was prepared using buffered peptone water. 20 μL aptamer-coupled beads were added to 1 mL of $10^4$ cfu/mL of *L. monocytogenes* and incubated for 30 minutes on a rocking platform. Different combinations of aptamer-coupled magnetic beads were also tested to determine if improvement in capture efficiency could be obtained compared to incubation with single aptamer-coupled magnetic beads. The magnetic beads were then collected using a magnetic particle stand and washed once in 1 mL PBS-T. The beads were re-suspended in 40 μL PBS-T and plated on chromogenic agar (RAPID L.mono; Bio-Rad).

Table 3 shows the capture efficiency of selected aptamer-coupled magnetic beads with the indicated concentrations of *Listeria monocytogenes* and sizes of magnetic beads. The capture efficiency was determined as the ratio of the number of CFU on the plate to the number of CFU used for incubation, and is provided as a percentage. Some aptamers (A8T and 610.2T) were synthesized with a biotin label attached to a 15-atom TEG spacer on the 5' end. The remaining aptamers were synthesized with a biotin label attached to a standard 6-atom spacer on the 5' end. Aptamer-coupled magnetic beads were added at 20 μL (for single aptamer) and 15 μL (for A8T/610.2/264.10 combination) volumes for incubation in pure culture. For combination aptamer-coupled magnetic beads, aptamers were coupled to magnetic beads individually and 5 μL each were combined into a single sample.

TABLE 3

| Aptamer | *L. monocytogenes* Concentration (cfu/mL) | Size of Magnetic Beads | Capture Efficiency (%) n = 3 |
|---|---|---|---|
| A8T | 10,000 | 300 nm | 2.3 ± 0.67 |
| A8 | 10,000 | 300 nm | 0.33 ± 0.06 |
| A16 | 10,000 | 300 nm | 0.26 ± 0.86 |
| A21 | 10,000 | 300 nm | 0.30 ± 0 |
| A26 | 10,000 | 300 nm | 0.30 ± 0 |
| 610.2T | 10,000 | 300 nm | 1.47 ± 0.23 |
| 610.2 | 10,000 | 300 nm | 1.37 ± 0.29 |
| 264.1 | 10,000 | 300 nm | 0.24 ± 0.08 |
| 264.3 | 10,000 | 300 nm | 0.33 ± 0.01 |
| 264.10 | 10,000 | 300 nm | 0.28 ± 0.02 |
| A8T/610.2/264.10 | 16,000 | 300 nm | >3.0 ± NA |
| A8T | 10,000 | 500 nm | 0.23 ± NA |
| A8T | 10,000 | 1 μm | 0.19 ± 0.13 |
| A8T | 10,000 | 2.8 μm | 0.10 ± NA |
| 610.2T | 10,000 | 1 μm | 0.12 ± 0.01 |

The ability of aptamer-coupled magnetic beads to capture *Listeria monocytogenes* in food was also tested. To compare sensitivity of these beads to commercially available anti-*Listeria* magnetic beads, 1, 6, and 60 CFU *Listeria monocytogenes* was incubated in 25 g turkey deli meat in 225 mL ½ Fraser broth (stomached for 2 minutes at 230 rpm) at 37° C. for 24 hours. A 1 mL aliquot was transferred to a microcentrifuge tube and 60 uL combination aptamer-coupled magnetic beads was added. The beads were incubated with the food sample for 30 minutes on a rocking platform. The magnetic beads were then collected using a magnetic particle stand and washed once in 1 mL PBS-T. The beads were re-suspended in 60 μL PBS-T and plated on chromogenic agar at 37° C. overnight. All plates had excessive quantities of colonies that indicated the ability of aptamer-coupled magnetic beads to capture 1 CFU *Listeria monocytogenes* in food after 24 hours of incubation.

In another embodiment, the disclosed aptamers are tested for their ability to capture *Listeria monocytogenes* when coupled to magnetic beads using a biosensor. A biosensor composed of giant magnetoresistive (GMR) materials can take advantage of the magnetic bead and utilize it as a label. Thin structures of alternating magnetic and nonmagnetic layers with a total thickness of a few hundred nanometers exhibit a phenomenon known as giant magnetoresistance. The resistance of microfabricated giant magnetoresistors is dependent on the strength of an external magnetic field. By passing a current through a strip of GMR material and measuring its resistance, local magnetic fields can be measured. This type of sensor can detect the presence of magnetic beads. A GMR sensor that can detect *Listeria* may consist of a chip with an aptamer or polyclonal antibody against *Listeria* patterned on its surface. In one embodiment, the aptamer magnetic beadcaptured *Listeria* is applied to this chip and is bound to the immobilized aptamer or polyclonal antibody. In another embodiment, a sample containing the target *Listeria* is applied to the chip followed by aptamer-coupled magnetic beads. Any beads that are not specifically bound to the chip are removed by applying a magnetic field gradient with the electromagnet and/or controlled laminar flow. The GMR sensor detects the remaining beads attached to the surface of the chip. The intensity of the signal indicates the concentration of *Listeria* present in the sample.

In another embodiment, the disclosed aptamers are tested for their ability to capture *Listeria monocytogenes* when coupled to magnetic beads using an ELISA screen.

In another embodiment, the disclosed aptamers are tested for their ability to capture *Listeria monocytogenes* when coupled to magnetic beads using PCR.

Use of Aptamers in Listeriosis Therapy or To Reduce Likelihood of Listeriosis

Disclosed aptamers that specifically bind the active site of the InlA, InlE, and Lmo0610 proteins that are involved in promoting *Listeria* infection would be expected to have the effect of inhibiting the development of listeriosis.

Therapeutic compositions of the aptamers may be administered parenterally by injection, although other effective administration forms, such as intraarticular injection, inhalant mists, orally active formulations, transdermal iontophoresis, or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parenteral administration in either unit dose or multidose form.

Once the therapeutic composition has been formulated, it may be stored in sterile vials as a solution, suspension, gel, emulsion, solid, or dehydrated or lyophilized powder. Such formulations may be stored either in a ready to use form or require reconstitution immediately prior to administration. The manner of administering formulations containing nucleic acid ligands for systemic delivery may be via subcutaneous, intramuscular, intravenous, intranasal, or vaginal or rectal suppository.

In some cases, nucleic acid sequences such as these aptamers are themselves susceptible to enzymatic degradation. This may be counteracted by administering the aptamers in a protected form.

One way in which this can be done is to bind the aptamers to a protective molecule in order to prevent degradation, as disclosed for example in U.S. Pat. No. 7,005,132. For example, an aptamer that specifically binds and inhibits InlA, InlE, and Lmo0610 is protected against enzymatic degradation by administration in specifically bound form. The specific binding partner of the anti-InlA, anti-InlE, or anti-Lmo0610 aptamer may either be a synthetic receptor selected from a combinatorial shape library or an oligonucleotide that hybridizes to the aptamer through Watson-Crick base pairing with a suitable degree of complementarity to yield quasi-stable hybrids that are dissociable in the presence of InlA, InlE, or Lmo0610. These oligonucleotides are generated by in vitro evolution from initial sequence segments complementary to different nucleotide sequences of the anti-InlA, anti-InlE, or anti-Lmo0610 aptamer. In this embodiment, at least one InlA, InlE, or Lmo0610 aptamer is selected for specific binding to a relatively conserved region of InlA, InlE, or Lmo0610 from a randomized pool or combinatorial shape library comprising oligonucleotides generated by in vitro evolution. Potentially useful shape libraries include, without limitation, populations of polymeric conformers prepared from random combinations of amino acids, nucleotides, carbohydrates, and other organic monomers. Selected synthetic receptors are first evaluated in vitro for effectiveness in protecting aptamers against enzymatic degradation through stability studies of corresponding prodrug complexes and control (unbound) aptamers. Synthetic receptors affording protection are then tested for their ability to efficiently deliver aptamers to therapeutic targets in vitro. Prodrug complexes comprising each selected aptamer specifically bound to each selected synthetic receptor are incubated alone and in combination with isolated preparations of InlA, InlE, or Lmo0610, and the rate, degree and duration of inhibition of infection are compared with control conditions (InlA, InlE, or Lmo0610 alone; InlA, InlE, or Lmo0610 plus aptamer(s); InlA, InlE, or Lmo0610 plus synthetic receptor(s)). Selected prodrug complexes and combinations are then tested for safety and efficacy in preclinical and clinical studies.

Example 1

Listeriosis Therapy

A patient having clinical indications of listeriosis is intravenously administered a dose of one of the aptamers shown in Table 1 in a dose of 0.5 to 50 mg/kg per day, such as 5 mg/kg per day for 1 to 30 days, e.g., 15 days. This may be administered in a single dose, or may be administered as a number of smaller doses over a 24-hour period: for example, three smaller doses at eight-hour intervals. Following treatment, a significant proportion of the InlA, InlE, or Lmo0610 protein is bound by the aptamer and the listeriosis infection is ameliorated.

Example 2

Reduction in Likelihood of Development of Listeriosis

A patient at risk for developing listeriosis (for example as a result of consuming food known to be or suspected of being contaminated with *Listeria monocytogenes*) is intravenously administered a dose of one of the aptamers shown in Table 1 in a dose of 0.5 to 50 mg/kg per day, such as 5 mg/kg per day for 1 to 30 days, e.g., 15 days. This may be administered in a single dose, or may be administered as a number of smaller doses over a 24-hour period: for example, three smaller doses at eight-hour intervals. Following treatment, a significant proportion of the InlA, InlE, or Lmo0610 protein is bound by the aptamer. The patient does not exhibit clinical manifestations of listeriosis, or exhibits only mild symptoms.

While specific embodiments of the invention have been described above, such embodiments should be considered illustrative of the invention only and not as limiting the invention as construed in accordance with the claims below.

What is claimed is:

1. An isolated aptamer comprising SEQ ID NO: 1.
2. An isolated aptamer comprising SEQ ID NO: 2.
3. An isolated aptamer comprising SEQ ID NO: 3.
4. An isolated aptamer comprising SEQ ID NO: 4, and wherein the aptamer is coupled to a solid support by a spacer comprising 6 or more atoms between said aptamer and said support.
5. The aptamer of claim 4, wherein the aptamer is coupled to a solid support by a spacer comprising 10 or more atoms between said aptamer and said support.
6. The aptamer of claim 5, wherein the aptamer is biotinylated.
7. The aptamer of claim 6, wherein the spacer is tetraethylene glycol.
8. An isolated aptamer comprising SEQ ID NO: 5.
9. An isolated aptamer comprising SEQ ID NO: 6.
10. An isolated aptamer comprising SEQ ID NO: 7.
11. An isolated aptamer comprising SEQ ID NO: 8.
12. A method of capturing *Listeria monocytogenes* that is present in a sample comprising exposing the sample to an aptamer according to any one of claims 1-4, 8-10, or 11 that specifically binds a protein selected from the group consisting of *Listeria monocytogenes* internalin A protein, *Listeria monocytogenes* internalin E protein, and *Listeria monocytogenes* 0610 protein.
13. The method of claim 12, wherein the aptamer is coupled to a magnetic bead.
14. The method of claim 13, wherein the magnetic bead is a bead with a diameter of less than 500 nm.
15. The method of claim 13, wherein the magnetic bead is a bead with a diameter of between 200 nm and 400 nm.
16. A method of assaying a sample for the presence of *Listeria monocytogenes*, comprising:
 exposing the sample to an aptamer according to any one of claims 1-4, 8-10, or 11 that specifically binds a protein selected from the group consisting of *Listeria monocytogenes* internalin A protein, *Listeria monocytogenes* internalin E protein, and *Listeria monocytogenes* 0610 protein; and determining that *Listeria monocytogenes* is present in the sample when the aptamer binds the protein present in the sample.

* * * * *

UNITED STATES PATENT AND TRADEMARK OFFICE
CERTIFICATE OF CORRECTION

| | |
|---|---|
| PATENT NO. | : 7,645,582 B2 |
| APPLICATION NO. | : 12/422971 |
| DATED | : January 12, 2010 |
| INVENTOR(S) | : Cindy Yamamoto and Toshit Sen |

It is certified that error appears in the above-identified patent and that said Letters Patent is hereby corrected as shown below:

On page 1, column 2, line 23, delete "haemagglutanin," and insert --haemagglutinin-- thereof.

At column 3, line 59, delete "hemagglutinin," and insert --haemagglutinin-- thereof.

At column 3, line 64, delete "PLos," and insert --PLoS-- thereof.

At column 5-6, line 2, delete "In1A," and insert --InlA-- thereof.

At column 5-6, line 3, delete "In1A," and insert --InlA-- thereof.

At column 5-6, line 4, delete "In1A," and insert --InlA-- thereof.

At column 5-6, line 5, delete "In1A," and insert --InlA-- thereof.

At column 5-6, line 7, delete "In1E," and insert --InlE-- thereof.

At column 5-6, line 8, delete "In1E," and insert --InlE-- thereof.

At column 5-6, line 9, delete "In1E," and insert --InlE-- thereof.

At column 6, line 44, delete "www2.," and insert --www.-- thereof.

At column 7-8, line 1, delete "In1A," and insert --InlA-- thereof.

At column 7-8, line 2, delete "In1A," and insert --InlA-- thereof.

At column 7-8, line 3, delete "In1E," and insert --InlE-- thereof.

At column 7-8, line 4, delete "In1E," and insert --InlE-- thereof.

At column 9, line 35, delete "μmol," and insert --pmol-- thereof.

Signed and Sealed this
Fifth Day of April, 2011

David J. Kappos
*Director of the United States Patent and Trademark Office*